(12) United States Patent
Pieri et al.

(10) Patent No.: US 12,171,570 B2
(45) Date of Patent: Dec. 24, 2024

(54) MULTI-SENSOR PATCH

(71) Applicant: GE Precision Healthcare LLC, Wauwatosa, WI (US)

(72) Inventors: Jean-Francois Pieri, Nottingham (GB); Steven M. Falk, Baltimore, MD (US)

(73) Assignee: GE Precisions Healthcare LLC, Wauwatosa, WI (US)

( * ) Notice: Subject to any disclaimer, the term of this patent is extended or adjusted under 35 U.S.C. 154(b) by 408 days.

(21) Appl. No.: 17/435,328

(22) PCT Filed: Apr. 16, 2020

(86) PCT No.: PCT/US2020/028515
§ 371 (c)(1),
(2) Date: Aug. 31, 2021

(87) PCT Pub. No.: WO2020/214812
PCT Pub. Date: Oct. 22, 2020

(65) Prior Publication Data
US 2022/0133213 A1     May 5, 2022

Related U.S. Application Data

(60) Provisional application No. 62/834,485, filed on Apr. 16, 2019.

(51) Int. Cl.
*A61B 5/00* (2006.01)
*A61B 5/01* (2006.01)
(Continued)

(52) U.S. Cl.
CPC .............. *A61B 5/4362* (2013.01); *A61B 5/01* (2013.01); *A61B 5/021* (2013.01);
(Continued)

(58) Field of Classification Search
None
See application file for complete search history.

(56) References Cited

U.S. PATENT DOCUMENTS 4,299,234 A * 11/1981 Epstein .............. A61B 5/02411
600/511
5,749,365 A * 5/1998 Magill ................. A61B 5/0205
128/903
(Continued)

FOREIGN PATENT DOCUMENTS

EP         2819574 B1    1/2019
WO    WO-2018102874 A1 *  6/2018 ........... A61B 5/0002

OTHER PUBLICATIONS

EP patent application 20792246.9 filed Oct. 5, 2021—extended Search Report issued Jan. 5, 2023; 5 pages.
(Continued)

*Primary Examiner* — Michael W Kahelin
*Assistant Examiner* — Luke M Stanley
(74) *Attorney, Agent, or Firm* — Andrus Intellectual Property Law, LLP

(57) ABSTRACT

A multi-sensor patch for simultaneous abdominal monitoring of maternal and fetal physiological data includes a multi-layer flexible substrate with a center region and a plurality of electrode regions. A conductive layer of the flexile substrate provides an electrical connection between each of the plurality of electrode regions and the center region. A plurality of electrodes are formed into the flexible substrate. At least one mechanical motion sensor is connected to the multi-layer flexible substrate. A module unit is connected to the conductive layer at the center region. The module unit includes a controller configured to receive biopotential physiological data from the plurality of electrodes and mechanical sensor data from the at least one auxiliary sensor. The controller calculates at least fetal heart (Continued)

rate, maternal heart rate, and uterine activity from the biopotential physiological data and from the mechanical sensor data.

22 Claims, 4 Drawing Sheets

(51) Int. Cl.
- *A61B 5/021* (2006.01)
- *A61B 5/024* (2006.01)
- *A61B 5/145* (2006.01)
- *A61B 5/259* (2021.01)
- *A61B 5/273* (2021.01)
- *A61B 5/344* (2021.01)
- *A61B 5/352* (2021.01)

(52) U.S. Cl.
CPC ...... *A61B 5/02411* (2013.01); *A61B 5/14542* (2013.01); *A61B 5/259* (2021.01); *A61B 5/273* (2021.01); *A61B 5/344* (2021.01); *A61B 5/352* (2021.01); *A61B 5/4356* (2013.01); *A61B 5/6833* (2013.01); *A61B 2562/0261* (2013.01); *A61B 2562/066* (2013.01)

(56) References Cited

U.S. PATENT DOCUMENTS

| | | | |
|---|---|---|---|
| 6,353,754 B1 | 3/2002 | Fischell et al. | |
| 6,385,473 B1 | 5/2002 | Haines et al. | |
| 6,434,418 B1* | 8/2002 | Neal | A61B 5/02411 600/511 |
| 7,865,233 B2* | 1/2011 | Haefner | A61B 5/7203 600/513 |
| 9,693,690 B2 | 7/2017 | Ater | |
| 9,717,412 B2 | 8/2017 | Roham et al. | |
| 2007/0239039 A1* | 10/2007 | Yang | A61B 5/332 600/483 |
| 2010/0280331 A1* | 11/2010 | Kaufman | A61B 5/0245 600/301 |
| 2012/0150010 A1* | 6/2012 | Hayes-Gill | A61B 5/721 600/382 |
| 2013/0137998 A1* | 5/2013 | Lange | G16H 50/30 600/587 |
| 2013/0281861 A1* | 10/2013 | Flomerfelt | A61B 8/02 600/483 |
| 2014/0091945 A1 | 4/2014 | Rivas et al. | |
| 2014/0330087 A1 | 11/2014 | Succi et al. | |
| 2015/0150538 A1* | 6/2015 | Reuter | A61B 5/113 600/301 |
| 2016/0157717 A1* | 6/2016 | Gaster | A61B 5/02416 600/301 |
| 2016/0262649 A1* | 9/2016 | Hayes-Gill | A61B 5/6833 |
| 2020/0187804 A1* | 6/2020 | Iyer | A61B 5/726 |

OTHER PUBLICATIONS

International Search Report and Written Opinion for International Application PCT/US20/28515 mailed Jul. 15, 2020.

* cited by examiner

MULTI-SENSOR PATCH

CROSS-REFERENCE TO RELATED APPLICATIONS

This application is the U.S. national stage application of International Application PCT/US20/28515, filed Apr. 16, 2020, which international application was published on Oct. 22, 2020, as International Publication WO 2020/214812 A1 in the English language. The International Application claims priority to U.S. Provisional Patent Application No. 62/834,485 filed Apr. 16, 2019.

BACKGROUND

The present disclosure relates to maternal and fetal monitoring. More specifically, the present disclosure relates to an apparatus and method for monitoring a plurality of physiological parameters of maternal and fetal patients.

Medical devices are known that can be used to detect a fetal electrocardiogram (fECG) without making physical contact with the fetus. Such devices use electrodes that are placed on the mother's skin to detect electrophysiological signals. The maternal electrocardiogram (mECG) will also tend to be detected by the electrodes, and it can be challenging to separate the fECG from the mECG. The electrical signals detected by the electrodes can be processed to determine: the fetal heart rate (from the fECG), the maternal heart rate (from the mECG). Maternal contractions, often referred to as uterine activity (UA), can be determined by electrohysterography (changes in electrical potential due to uterine contractions) which can be detected by the electrodes.

WO2009/150440 discloses a multi-electrode patch for use in fetal heart rate monitoring, the patch comprising a flexible substrate attachable to the skin of a pregnant subject. Three sensing electrodes are positioned on the flexible substructure to approximate an arc that is substantially the same length as the arc formed by a uterus fundus of a pregnant subject. Connection ports are provided by which each sensing electrode may be connected to a fetal heart rate monitor which receives the electrical signals from the electrodes and determines the fetal heart rate from the fECG, maternal heart rate from the mECG, and UA from the electrohysterogram. A multi-electrode patch is disclosed that includes integrated circuitry configured to amplify and filter a detected fECG signal.

EP 1 854 403 discloses a radial electrode assembly for monitoring fECG and mECG signals. The assembly comprises a flexible substrate defining a central focal point, and a plurality of electrodes disposed on the periphery of the flexible substrate, at a substantially equal fixed radial distance from the focal point.

US20160262649 discloses a multi-electrode patch for abdominal electrophysiological detection. The patch has a flexible substrate interconnecting multiple electrodes and a module unit for removably engaging with an electronic readout device for detecting a maternal and/or fetal electrophysiological signal from the electrodes. The module has a mechanical module unit for removable mechanical engagement with a housing of the readout device, and an electrical module unit for making an electrical connection from the electrodes to the readout device. The patch may be flexible in a manner that allows variation in the relative positioning between the electrodes.

Although the solutions noted above can be used for maternal and fetal monitoring, such systems are limited to monitoring ECG and ElectroHysterogram, and more robust patient monitoring is desired.

BRIEF DISCLOSURE

An exemplary embodiment of a multi-sensor patch for simultaneous abdominal monitoring of maternal and fetal physiological data includes a multi-layer flexible substrate. The multi-layer flexible substrate includes a center region and a plurality of electrode regions. A conductive layer of the flexible substrate providing an electrical connection between each of the plurality of electrode regions and the center region. A plurality of electrodes are formed into the flexible substrate. An electrode of the plurality of electrodes is located in each of the electrode regions. At least one mechanical motion sensor is connected to the multi-layer flexible substrate. A module unit is connected to the conductive layer at the center region. The module unit is configured to receive biopotential physiological data from the plurality of electrodes and mechanical sensor data from the at least one auxiliary sensor. The module unit calculates at least fetal heart rate (fHR), maternal heart rate (mHR), and uterine activity (UA) from the biopotential physiological data and from the mechanical sensor data.

In further exemplary embodiments of the multi-sensor patch, the at least one auxiliary sensor is a mechanical motion sensor and the module unit calculates a contraction strength from at least the mechanical sensor data. The plurality of electrodes, the conductive layer, and the at least one mechanical motion sensor may be printed from conductive ink. The at least one mechanical motion sensor may be a microphone. The at least one mechanical motion sensor may be a piezoelectric sensor. The physiological data from the piezoelectric sensor may be used by the module unit to calculate the fHR, mHR, and UA. The at least one mechanical motion sensor may include a strain gauge. The module unit may use the mechanical sensor data from the strain gauge to further calculate UA. In combination with the strain gauge the at least one mechanical motion sensor may include a microphone. The module unit may further use the mechanical sensor data from the microphone to further calculate fHR and mHR.

In still further exemplary embodiments at least one auxiliary sensor is located in the module unit. The at least one auxiliary sensor located in the module unit may include an ultrasound, a pulse oximeter, or a temperature sensor. The module unit may further calculate a rate from the biopotential physiological data and the mechanical sensor data. The module unit may further be configured to receive an input selection from a user. Upon receipt of such input selection, the module unit may switch from a calculation of UA that includes the biopotential physiological data to a calculation of UA based upon the mechanical sensor data while producing a calculated UA output in a real-time or near real-time refresh rate.

In further examples of the multi-sensor patch, the controller operates to select segments of the at least one of the biopotential physiological signals and mechanical physiological signals. Mechanical physiological signals are those physiological signals which reflect mechanical properties of the patient as opposed to electrical properties. Such mechanical properties which may be detected by mechanical sensors. Mechanical sensor signals may represent acoustic, transmission, reflectivity, temperature or other physical properties of the patient.

The controller operates to create a patient-specific model from the selected segments. The controller may operate to identify fetal R-waves in the biopotential physiological signals and to select segments of the mechanical sensor signals corresponding to fetal heartbeats in the mechanical sensor signals. The patient-specific model may be a heartbeat model of a fetal patient. The controller may apply the patient-specific model to the mechanical sensor signals to identify a search interval within a corresponding portion of the biopotential physiological signals for fECG detection. The controller may apply the patient-specific model to the mechanical sensor signals to improve detection of fetal heart motions. The controller may operate to identify maternal R-waves in the biopotential physiological signals and to select segments of the mechanical sensor signals corresponding to maternal heartbeats in the mechanical sensor signals. The patient-specific model may be a heartbeat model of a maternal patient. The controller may operate to apply the patient-specific model to the mechanical sensor signals to remove maternal contribution to the mechanical sensor signals. The controller may operate to compare the biopotential physiological signals and the mechanical sensor signals to reject false positive detections of contractions in UA determinations from the biopotential physiological signals.

An example of a multi-sensor patch for simultaneous abdominal monitoring of maternal and fetal physiological data includes a multi-layer flexible substrate with a center region and a plurality of electrode regions. A conductive layer of the flexile substrate provides an electrical connection between each of the plurality of electrode regions and the center region. A plurality of electrodes are formed into the flexible substrate. At least one mechanical motion sensor is connected to the multi-layer flexible substrate. A module unit is connected to the conductive layer at the center region. The module unit includes a controller configured to receive biopotential physiological data from the plurality of electrodes and mechanical sensor data from the at least one auxiliary sensor. The controller calculates at least fetal heart rate, maternal heart rate, and uterine activity from the biopotential physiological data and from the mechanical sensor data.

Further examples of the multi-sensor patch include the at least one auxiliary sensor is a mechanical motion sensor and the controller calculates a contraction strength from at least the mechanical sensor data. The plurality of electrodes, the conductive layer, and the at least one mechanical motion sensor may be printed from conductive ink. The at least one mechanical motion sensor may include a microphone. The at least one mechanical motion sensor may include a piezoelectric sensor. Mechanical sensor data from the piezoelectric sensor may be used by the controller in calculation of the fHR, mHR, and UA. The at least one mechanical motion sensor may include a strain gauge and the controller uses the mechanical sensor data from the strain gauge to further calculate UA. The at least one mechanical motion sensor may include a microphone and the controller uses the mechanical sensor data from the microphone to further calculate fHR and mHR. At least one auxiliary sensor may be located in the module unit and may include at least one of an ultrasound, a pulse oximeter, or a thermometer. The controller may calculate a respiration rate from the biopotential physiological data and the mechanical sensor data. The controller may be configured to receive an input selection from a user wherein upon receipt of such input selection, the controller switches from a calculation of UA that includes the biopotential physiological data to a calculation of UA based upon the mechanical sensor data while producing a calculated UA output in a real time or near real-time refresh rate. Mechanical sensor data from the microphone sensor may be used by the controller in calculation of the fHR and mHR.

The controller may further be configured to receive an input selection from a user and upon receipt of such input selection, the controller switches from a calculation of UA that includes the biopotential physiological data to a calculation of UA based upon the mechanical sensor data while producing a calculated UA and mHR output in a real time or near real-time refresh rate. At least one auxiliary sensor may include a pulse oximeter and physiological data from the pulse oximeter is used by the controller in combination with the biopotential physiological data to calculate maternal blood pressure. The controller may operate to select segments of the at least one of the biopotential physiological signals and mechanical sensor signals and to create a patient specific model from the selected segments. The controller may operate to identify fetal R-waves in the biopotential physiological signals and to select segments of the mechanical sensor signals corresponding to fetal heart beats in the mechanical sensor signals. The patient specific model may be a heartbeat model of a fetal patient. The controller may apply the patient specific model to the mechanical sensor signals to identify a search interval within a corresponding portion of the biopotential physiological signals for fECG detection. The controller may apply the patient specific model to the mechanical sensor signals to identify fetal heart motion and determine fetal heart rate. The controller may operate to identify maternal R-waves in the biopotential physiological signals and to select segments of the mechanical sensor signals corresponding to maternal heart beats in the mechanical sensor signals. The patient specific model may be a heartbeat model of a maternal patient. The controller may operate to apply the patient specific model to the mechanical sensor signals to remove maternal contribution to the mechanical sensor signals. The controller may operate to compare the biopotential physiological signals and the mechanical sensor signals to reject false positive detections of contractions in UA determinations from the biopotential physiological signals. The controller may conjunctly use the biopotential physiological signals and the mechanical sensor signals to detect uterine contraction. The auxiliary sensor may include a temperature sensor, and mechanical sensor data from the temperature sensor is used by the controller with the calculated mHR to determine an estimate of maternal core temperature.

DETAILED DISCLOSURE

Figure 1:
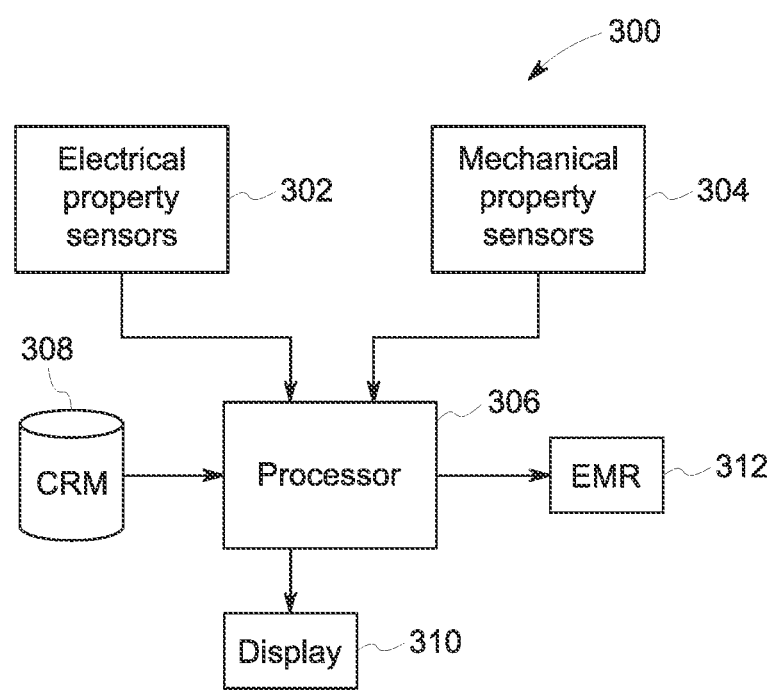
FIG. 1 is a system diagram of an exemplary embodiment of a system for monitoring a maternal patient and a fetal patient.

Common solutions for monitoring of maternal and fetal patients, include the use of ultrasound to detect fetal heart rate (fHR) and maternal heart rate (mHR) and a tocodynamometer to detect uterine activity. As noted above, electrode based solutions are available, although there are limitations to biopotential based systems. Currently, biopotential maternal and fetal monitors exemplarily use five silver/silver chloride wet electrodes to collect biopotentials from which measurements of fHR, mHR, as well as uterine activity are derived by computer processing of the collected biopotentials which include electrocardiographic data of both the maternal and fetal patients as well as uterine electromyographic data from which contractions are identified.

However, while the available electrode based solutions have advantages of disposability and ease of use, the present inventors have identified problems with the available systems that can be improved upon. It has been observed by the Inventors that the fHR as measured by the collected biopotentials can be lost when the fetus us surrounded by too much vernix caseosa. The vernix caseosa, or vernix, is the fatty deposit around the fetal patient which helps to protect the fetus during birth. Dependent upon the thickness and distribution of the vernix and position of the patient, this can lead to signal loss of the fetal ECG from which the fetal heart rate is derived. The fetal ECG can also be lost if there is a significant amount of skeletal electromyogram (EMG) noise. These signal loses may be relatively short in duration, but can be unpredictable in occurrence and may occur at inopportune times or may lead to unnecessary concern or worry among the maternal patient and/or caregivers.

Additionally, while biopotential measurement has been shown to be effective in the detection of contraction occurrences, the biopotential measurements have limited ability to detect contraction strength. At best, biopotentials may serve as a basis for comparative presentations of contraction strength without an ability for calibration or baseline contraction strength determinations.

Finally, while currently available biopotential measurements of maternal and fetal heart rate as well as uterine activity are found to be accurate, due to the volume of biopotentials simultaneously acquired by such electrodes, intensive signal processing is required to isolate fHR, mHR, and UA from the collected signals. Due to this signal processing, the reported fHR, mHR, and UA are often presented on a delay. While in many patient monitoring settings this delay is acceptable as the fHR, mHR, and UA parameters are used as a general evaluation of fetal and maternal patient health, as well as the progression of labor, in some instances, patient information in real-time or near real-time is desired. An example of one such time in the care for the fetal and maternal patients, is during the placement of the epidural catheter. Due to the nature of epidural catheter placement into communication with the epidural space of the spine, real-time or near real-time identification of uterine activity it desired such as to avoid or limit maternal patient movement during the placement of the epidural catheter.

Therefore, the inventors have discovered that it is desirable to address the foregoing problems with current biopotential monitoring fetal and maternal patient monitoring systems, while maintaining a convenient, comfortable, and disposable patch form.

The biopotential base maternal and fetal monitor can thus be improved by the incorporation of one or more systems to detect mechanical motion of the maternal and fetal patients and to detect the mechanical motion of the maternal abdomen during uterine contraction.

As will be described in further detail herein, the combination of biopotential data and mechanical motion data provides for improved monitoring of fetal and maternal health in addition to addressing all of the problems identified above. Maternal and/or fetal patient-specific models can be created as described in further detail herein through the use of determinations from one signal as the true or confirming signal to extract segments of another corresponding signal for model development. Models created over time through learning between the signals from two types of sensors can be used to enhance the individual performance of fHR, mHR, or UA determinations made from two different signal types. One example includes the use of an exact time location of an mECG wave to build an acoustic model of the maternal heart sound from the mechanical sensor signal and subsequently use that maternal acoustic model to remove the maternal hear sound from the overall acoustic signal to isolate and enhance the fetal mechanical sound and resulting fHR determination therefrom. Another example includes the use of time periods of simultaneous good fECG detection from the electrical sensor with the acoustic signal to build an acoustic model of the fetal heart sound and use that acoustic model to enhance fHR detection from the mechanical sensor during periods where fECG cannot be detected on the electrical sensor. A further example uses timing information from the mechanical sensor signal related to fetal movement to improve UA contraction determinations from the biopotential signal by reducing fetal movement false positives from the contraction determination.

FIG. 1 depicts a system diagram of an exemplary embodiment of a monitoring system 300 for maternal and fetal patients. The system 300 is provided in schematic form and it will be recognized by a person of ordinary skill in the art that in such system 300 may be implemented in a variety of manners, including the distribution and interconnection of components provided in FIG. 1 as so much as various components may be provided in one or more physical devices while being communicatively connected generally in the manner as shown in FIG. 1. As noted above, the system 300 includes electrical property sensors 302, for example, the biopotential electrodes as disclosed above as well as will be described in further detail herein. These electrical property sensors 302 collect biopotentials from the skin of the maternal patient, which include biopotential signals from both the maternal and fetal patients.

The system 300 also includes at least one if not a plurality of mechanical property sensors 304 as will be described in further detail herein. The mechanical property sensors 304 may include, but are not limited to, ultrasound sensors, microphones, accelerometers, piezoelectric sensors, and strain gauges, and others as will be recognized by a person of ordinary skill in the art. The mechanical property sensors 304 are used to obtain signals indicative of mechanical motion by the maternal and/or fetal patients.

The signals obtained by the electrical property sensors 302 and the mechanical property sensors 304 are provided to a controller 306. The controller 306 may be any of a variety of controllers, microcontrollers, processors, or integrated circuits as known in the art of physiological sensing for collection and/or analysis of physiological data. The controller 306 is able to collect data from the sensors either in analog or digital format. In embodiments where the data is collected in analog format, an internal or external analog converter can be used. The controller 306 is communicatively connected to a computer-readable medium (CRM) 308 which is a non-transitory computer-readable medium upon which computer-readable code embodying software programs containing algorithm and/or software modules containing algorithms which upon execution by the controller 306 cause the controller to carry out the calculations and functions as described in further detail herein. The CRM 308 may be internal or external to the controller 306. In exemplary embodiments, the software and software modules as executed by the controller 306 are such as to isolate and analyze particular signals within the signals obtained from the electrical property sensors 302 as well as those obtained from the mechanical property sensors 304 in order to produce calculations of various output physiological parameters of the patient as described herein based upon the isolated and analyzed signals from the electrical property sensors 302 and/or mechanical property sensors 304. The controller 306 provides the calculated physiological parameter values to a display 310 which may operate to present one or more of the calculated values in a visually perceptible manner or stored at a patient electronic medical record (EMR) 312, stored at a non-transient computer data storage medium. The controller 306 may provide the calculated physiological parameter values across a wired or wireless connection and therefore, the display 310 or the EMR 312 may be physically connected to the controller 306, or may be located remote from the controller 306.

As noted above, it will be recognized that in embodiments, the electrical property sensors 302 and mechanical property sensors 304 may be integrated into the same patch of sensors as will be described in further detail herein, or may be provided as separate components. Additionally, the controller 306 and/or computer-readable medium 308 may be integrated with such a patch containing the electrical property sensors 302 and the mechanical property sensors 304 while in other embodiments, the system 300 may include additional instrumentation such as to transmit the signals acquired from the electrical property sensors 302 and the mechanical property sensors 304 to be controller 306 which may be located remotely from the sensor. Still further configurations of the components as depicted in the system 300 as well as those system which include more or fewer components than those depicted in FIG. 1, will be recognized form the present disclosure while remaining within the scope of the present disclosure.

Figure 2:
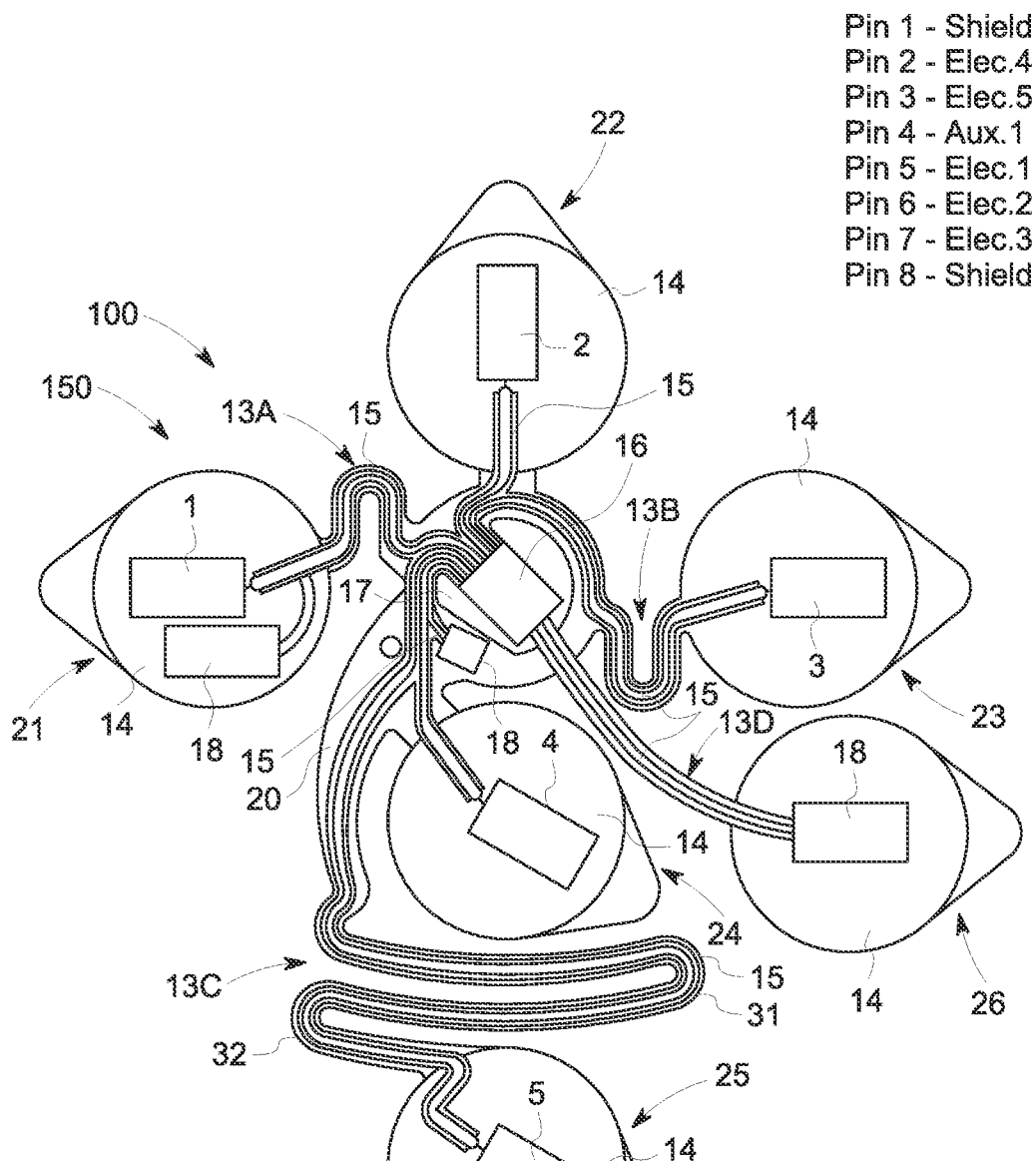
FIG. 2 is a layout diagram of an exemplary embodiment of a patch.

Referring to FIG. 2, a patch 150 exemplary of embodiments is shown. The patch 150 includes a flexible substrate 100, viewed from the side that is to be facing the abdomen, in use. The flexible substrate 100 comprises a plurality of layers 6-12. The layers 6-12 are patterned so as to define the shape of the substrate 100, and to form electrodes 1-5. Each electrode 1-5 is connected via a conducting track 15 to a connection hub 16, for electrically connecting electrodes 1-5 to a readout device (not shown). In embodiments as represented in FIG. 1, the substrate 100 may further be shaped to provide for a plurality of sensors, including, and in addition to electrodes 1-5. The plurality of sensors, as described in further detail herein may include at least one auxiliary sensor 18, although in embodiments more auxiliary sensors 18 may be found in the plurality of sensors. In embodiments, the conducting track 15 may be provided to electrically connect the one or more auxiliary sensors 18 to the connection hub 16. As previously noted, the one or more auxiliary sensors 18 may include one or more types of sensors configured to produce a signal indicative of the mechanical motion of the fetal patient and/or the maternal patient. Non-limiting embodiments of mechanical motion of the fetal patient may include fetal motion and/or kick counting, or fetal heart rate as monitored by fetal heart sounds, fetal heart movement, or fetal blood movement. Non-limiting embodiments of mechanical motion of the maternal patient may include maternal respiration movement or sounds, maternal heart sounds, maternal blood movement or sound, and maternal uterine contractions.

The electrodes 1-5 and/or the conducting tracks 15 and/or the auxiliary sensor 18 are formed from the signal layer 12, which includes silver ink or another material with the electrical and/or mechanical properties to form a sensor in the signal layer. For example, the conducting film used can be silver chloride which provides a good stoichiometric match to saline based electrode gels. A silver-containing ink may be used in particular to print the conducting tracks 15 and/or signal layer 12. As noted above, in exemplary and non-limiting embodiments, the auxiliary sensor 18, may be any of a strain gauge, a piezoelectric sensor, an accelerometer, a microphone, temperature sensor, SpO2 sensor, an ultrasound Doppler, a capacitive micromachined ultrasonic transducer, or other sensors as will be recognized by a person of ordinary skill in the art in view of the present disclosure. As will be discussed in further detail herein, the auxiliary sensor 18 may be formed from the signal layer 12 and/or printed from the silver containing ink. In other embodiments, the auxiliary sensor 18 may be a separately formed component and the signal layer 12 provides the conducting track 15 and/or a mounting or connection pad or contact.

Embodiments of the auxiliary sensor may be located in a variety of locations within the patch 150. FIG. 2 provides three exemplary locations for the auxiliary sensor 18, these include placing the auxiliary sensor 18 in one or more of the patch regions 21-25 which contain the electrodes 1-5, in a central patch region 20 of the substrate, or in a dedicated sensor patch region 26 of the substrate 100. However, it will be recognized that embodiments may include an auxiliary sensor 18 at one of these locations, at all of these locations, or at other locations. Such other locations may include, but are not limited to within the connection hub 16 or within the readout device 200 as will be described in further detail herein, for example with respect to FIGS. 3 and 4.

An insulating dielectric layer 11A, 11B is arranged on each respective side of the signal layer 12. The insulating dielectric layers 11A, 11B have a similar pattern to the conducting tracks 15 of the signal layer 12. The insulating layers 11A, 11B substantially overlay the conducting tracks 15, and are oversized relative thereto. The insulating layers 11A, 11B completely cover the conducting tracks between the plurality of sensors and the connection hub 16, while leaving the signal layer 12 exposed at the electrodes, auxiliary sensor(s) and connection hub 16.

A graphite layer 10A, 10B is in contact with each of the respective dielectric layers 11A, 11B. The graphite layers 11A, 11B substantially overlay the respective insulating layer 11A, 11B, and are oversized relative thereto.

A first conducting shield layer 9A is in contact with the graphite layer 10A, and a second conducting shield layer 9B is in contact with the optional graphite layer 10B. The first and second conducting shield layers 9A, 9B substantially conform to the shape of their respective graphite layers 11A, 11B. The graphite layers 10A, 10B may reduce triboelectric charging of the respective shield layers 9A, 9B.

In some embodiments the graphite layers 10A, 10B may be omitted.

A further insulating dielectric layer 8 is in contact with the first conducting shield layer 9A, and an insulating overlaminate 6A is in contact with this layer 8. An insulating base layer 6B is also in contact with the second conducting shield layer 9B. The overlaminate 6A and base layer 6B are configured to substantially encapsulate the other layers of the substrate, except, for example in an area about each of the plurality of sensors, if such sensors require a skin interface. In the area about the sensors that require a skin interface, the signal layer 12 may be exposed so that such sensors, for example, electrodes 1-5 can make contact with an underlying surface of the maternal patient's skin. The insulating overlaminate 6A and base layer 6B may comprise a plastics material, such as polyester. The insulating dielectric layers 8, 11A, 11B may comprise a plastics material, such as polyester or polyimide.

The base layer 6B exemplarily defines the external shape of the flexible substrate 100, and includes patch regions 21-26 exemplarily corresponding with each sensor. These sensors may include electrodes 1-5 and auxiliary sensor 1. While the electrodes 1-5 and auxiliary sensor 1 are depicted as substantially rectangular, it will be recognized that the sensors may be arranged in any shape as is suitable for the measurement obtained by such sensors. The patch regions 21-26 extend about the respective sensors associated therein. The patch regions 21-26 may be provided with an adhesive film around their perimeter, so that each patch region 21-26 can be adhered to the skin of a subject. For sensors of the plurality of sensors for which a conductive connection between the sensor and the skin of the maternal patient is needed, a conducting medium (for example ECG or acoustic gel) is preferably disposed between the sensors and the skin of the subject, thereby signally coupling the sensors to the skin of the maternal patient.

Each patch region 21-26 may include a lobe, or flap, that is substantially free from adhesive film or conducting medium and protrudes from the patch region 21-26. The lobe can be used by a clinician to hold the respective patch region 21-26 for placement, movement, or detachment of the patch region 21-26 on the maternal patient's body. Clinician gripping of the lobe helps to prevent fouling or contamination of any adhesive or conducting medium of the patch regions 21-26 or cross-contamination to the clinician from handling a patch region 21-26 that has been used.

For any polymer layer described above, a PET material may be used and has been found to provide useful properties, i.e. resilience, for avoiding breakage of the signal layer 12 during flexing of the patch in use. The material thickness of the polymer/PET layer(s) may be matched to the properties of the signal conducting layer 12 to prevent deformation of the tracks in a manner that is likely to lead to a break in the signal layer 12.

The substrate 100 comprises a reference feature 17, for lining up with an umbilicus or other suitably recognizable feature of the subject. In this case, the reference feature 17 is defined by an aperture in the flexible substrate 100. In other embodiments the reference feature 17 may be a vertex, pointer or transparent region forming in the flexible substrate 100. The reference feature 17 may be associated with an adjacent adhesive region, by which the reference feature 17 can be secured to the subject, for example, adjacent to the umbilicus. As depicted in FIG. 2, the auxiliary sensor 18 may be located at a region about the reference feature 17. In embodiments when the reference feature 17 is centrally located to the patch regions 21-26, the region about the reference feature 17 may provide also provide a central and desirable location from which to measure the mechanical movement of the maternal patient and/or the fetal patient. In still further embodiments wherein multiple auxiliary sensors 18 are used, an auxiliary sensor located in the region of the reference feature 17 can be used as a reference sensor for example for noise cancellation or as an active electrode for injecting a mechanical, e.g. acoustic signal into the maternal and fetal patients.

The structure lends itself to a straightforward method of application. For example, the reference feature 17 may be secured at a reference point on the patient using the associated adhesive region. The electrodes 1-5 and respectively on regions 21-25 and auxiliary sensor 18 on region 26 can subsequently be moved away from the abdomen to prepare the skin. For example each patch region 21-26 can then be placed in turn around the abdomen with, if necessary, suitable abrasive skin preparation. It will be recognized that while electrodes 1-5 may require a suitable electrode-skin interface, the auxiliary sensor may require such an interface, for example with an ultrasound Doppler, a capacitive micromachined ultrasonic transducer, or a piezoelectric sensor, while other embodiments of auxiliary sensors, for example, accelerometers, microphones, or strain gauges do not require the same electrical and/or acoustical interface with the maternal skin. Once any skin preparation, if needed, and the subsequent placement of an electrode 1-5 or auxiliary sensor has been completed the impedance of the connection between the electrode 1-5 and the patient may be measured by an electronic readout device 200 (shown in FIG. 7). If the impedance is above a desired value, further preparation of the skin may be carried out to reduce the impedance to below the desired value. The desired value may, for example, be 5 kOhms. When the impedance is below the desired value, the skin region for the next electrode may be prepared by abrading the skin and the electrode subsequently applied electrode, and the impedance tested. This method may be repeated until all of the electrodes are successfully applied.

Figure 3:
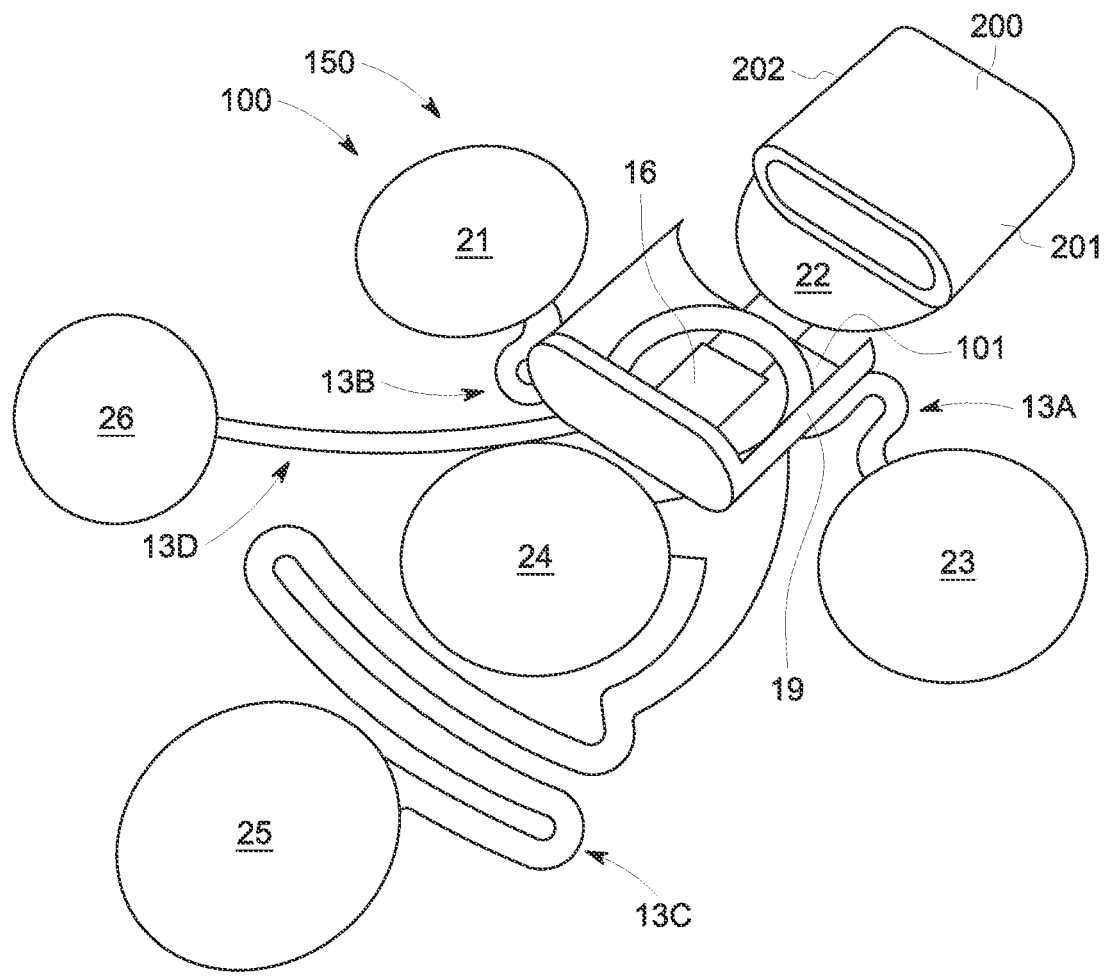
FIG. 3 is a perspective view of an exemplary embodiment of a patch and readout device.

FIG. 3 shows a top view of an exemplary embodiment of a patch 150 as depicted in FIG. 2. In this embodiment, the mechanical module unit 19 is affixed to the substrate 100 adjacent to the electrical module unit 16, as previously shown in FIG. 2. The patch 150 is shown with a separate electronic readout device 200 for detecting signals from the electrodes 1-5 and at least one auxiliary sensor 18 of the patch 150. In embodiments as described in further detail herein with respect to FIG. 4, the readout device 200 may include a processor or other processing electronics to analyze the detected signals and to produce physiological data of the fetal and maternal patients. In still further embodiments, the readout device 200 may rather serve a communicative function, providing wireless communication of the detected signals from the sensors of the patch 150 to a computer processor located remote from the patch 150. The remotely located computer processor may perform the same functions as described herein to analyze the detected signals to produce physiological data of the fetal patent and the maternal patient. In embodiments, the remotely located computer processor may be located in a same room as the maternal patient, while in other embodiments the remotely located computer processor may be a cloud or networked computer processing system wherein the detected signals are transmitted to a location further away for processing. In such embodiments, any calculated physiological data may be returned back locally for presentation to caregivers and/or the maternal patient.

The mechanical module 19 comprises a cradle for receiving the readout device housing 201 of the readout device 200. The housing 201 is removably received and held within the cradle, which allows movement of the housing 201 only in the direction of insertion/removal. The cradle comprises a stop, and the readout device 200 is fully engaged with the mechanical module unit 19 when the housing 201 is in contact with the stop. The mechanical module 19 further comprises a latch or catch to retain the readout device housing 201 in contact with the stop. In this embodiment the latch or catch comprises a magnetic catch. A permanent magnet is provided on either (or both) of the mechanical module 19 and housing 201, which attracts a corresponding magnet (or ferromagnetic element) on the other of the mechanical module 19 or housing 201. In alternative embodiments, a hook and loop arrangement (e.g. Velcro) may be used to secure the readout device 200 to the patch 150. In an embodiment, the magnetic catch can be used to avoid incorrect positioning of the mechanical module.

In embodiments, the readout device 200 may also include one or more auxiliary sensors as described either above or in further detail herein. Auxiliary sensors may be located in the readout device 200, particularly those auxiliary sensors which may suitably operate without an acoustic or electric connection to the maternal patient's skin. Such sensors may exemplarily include an accelerometer. In other embodiments, the readout device 200 may include a microphone, a Doppler ultrasound sensor, or a capacitive micromachined ultrasonic transducer either to collect sounds from the maternal patient or to collect ambient sounds for noise cancellation from signals obtained from a microphone arranged in the patch 150 to collect sounds of the maternal and fetal patients.

When the readout device housing 201 is fully engaged with the mechanical module 19, an electrical module 204 (shown in FIG. 5) of the readout device 200 is in electrical engagement with the electrical module 16 of the patch 150. The electrical module 204 of the readout device 200 may conveniently comprise a plurality of contacts mounted on resiliently deformable members (e.g. spring loaded contact pins).

The readout device 200 is preferably configured to calculate an output at least one of a: fHR, fECG, mHR, mECG, or UA. Preferably the readout device is configured to output any two, three, four, or all five of the above. The readout device is preferably configured to transmit the output, so that it can be monitored. As described in further detail herein, the readout device can calculate the above parameters from the detected biopotentials. Additionally, the readout device can calculate fHR, mHR, or UA from the signals of the at least one auxiliary sensor. In still further exemplary embodiments, fHR, mHR, and UA are calculated by using both types of signals. These calculations may weight the contribution of the biopotential signals and the auxiliary signals to the calculations of fHR, mHR, and UA while in other embodiments, the signal strengths or quality may be determined and the calculations of fHR, mHR, and UA based upon the different signals selected based upon the input signal quality. In still further embodiments the calculations may be used in combination, for example, the biopotential determination of UA may be used to help identify UA occurrence in the mechanical sensor signal while contraction strength is calculated from the mechanical sensor signal.

As previously noted, the biopotential analysis of fHR, mHR, and UA are known to be accurate, but processing systems to calculate each of these parameters from the same signals may result in a delay in the output to ensure that a high-quality calculation is made. However, during some medical procedures, for example, an epidural catheterization, real-time, or near real-time indications of UA and/or contraction strength, and possibly as well as fHR and mHR may be desired. In an example, the combination of the signals from the biopotential sensors and the auxiliary sensors can be used to operate in an "epidural mode", producing a real-time or near real-time output of physiological parameters. In one embodiment, the signals from the biopotential sensors and the auxiliary sensors are used to increase the input information and increasing the reliability of the output produced using real-time or near-real time signal processing techniques. In another embodiment, the biopotentials are used to produce the calculations of fHR and mHR, while the auxiliary sensor signal is used to produce the calculations of the UA and contraction strength. By segmenting the determinations made from each signal, signal processing can be more specifically focused, resulting in faster calculations of each of the physiological parameter values.

In an embodiment, with detection of fHR and mHR from two different physiological properties (e.g. biopotential and mechanical motion), a comparison between these determinations can be made to further evaluate fetal and/or maternal health. By comparing the onset and occurrence of heartbeats as detected based upon electrical activity and mechanical motion, discontinuity between these two physiological observations, for example, electrical impulses that to produce an expected mechanical result can be observed. Detection of this anomaly can provide an early warning of serious medical conditions. In another embodiment, an estimate of maternal blood pressure can be calculated from a comparison of the maternal pulse from the mECG and maternal pulse from the pulse oximetry sensor.

As noted above, the electrical detection of fECG is typically more accurate than the mechanical detection of fetal heart sound. The fECG signal tends to be more fiducial due to the sharp R-wave shape that is used for detection. However, the detection of fetal heart sounds may be obtained in a faster real-time or near-real-time processing or may be available at times during patient monitoring when the detection of one or more biopotentials required to calculate fECG are not available. Therefore, in examples, heart rate determinations based upon the measurements from the one or more mechanical property sensors can be complementary to the detection of fECG.

In examples, during operation, the processor 306 uses synchronization between the collected biopotential signals and the mechanical sensor signals to improve detection of the corresponding parameter. In one example, detection of heartbeats in mECG or fECG can be applied to the corresponding mechanical sensor signal to improve determination of mHR or fHR from the mechanical sensor signal. In another example, detection of heartbeats in the mechanical sensor signals can be applied to the corresponding biopotential signals to improve determination of mHR or fHR from the biopotential signals.

In still further examples, synchronized learning between the signals from the electrical property sensors 302 and the signals from the mechanical property sensors 304, to create a patient-specific model for use in future detection of heart rates based solely upon the signals of the mechanical property sensors (e.g. fetal heart sounds). During times when fECG can be detected (e.g. during periods of low skeletal electrical noise), the fECG R-wave or QRS complex can be determined from the fECG signal. This determination provides a precise fHR and the period between fetal heartbeats. With the simultaneous collection of the fetal heart sounds with a mechanical property sensor, exemplarily a microphone, the corresponding timing of the fetal heartbeats from the R-wave or the QRS complex of the fECG can be used in analysis of the fetal heart sounds.

In an example, using the timing provided by the fECG, the fetal heart sound signal is windowed into segments relative to the fECG. In an example, a window of the fetal heart sound signal is taken centered on the R-wave or QRS complex of the fECG. The window may have any temporal width up to the intra-beat period of the fetus at that time. It will be recognized that in further examples, the temporal width of the window may be of a shorter or longer time duration. The temporal width of the window may further be skewed relative to the R-wave or QRS complex of the fECG extending either further before or further after the reference point of the R-wave or QRS complex.

The segments of the fetal heart sound signal, which are obtained when the fECG signal is also available, are then used to create a model of the heart sounds of the fetal patient in the time or frequency domain. This model of the heart sounds is specific to the fetal patient and, when used to determine fHR from the fetal heart sound signal may be more accurate in determining an intra-beat heart rate compared to using other signal processing techniques, for example, autocorrelation, which results in an average value for fHR.

In examples, the fetal heart sound model is created (and updated) while quality data is obtained from both the fECG and the fetal heart sound signal. Then when fECG is lost (e.g. during a period of high skeletal noise) fHR can be determined directly from the fetal heart sound signal by applying the fetal heart sound model to the fetal heart sound signal.

In further examples, the use of fECG and the fetal heart sound signal may be reversed. Some patients, with a large amount of vernix around the fetus, may exhibit a higher quality fetal heart sound signal than the fetal biopotentials and resulting fECG. In such cases, the heart sound signal may be used to similarly detect the onset of each fECG beat.

The combined use of the electrical property sensors and the mechanical property sensors in providing enhanced signal analysis through the creation of patient-specific models can also be used to improve the detection of maternal parameters as well. A similar technique as described above can be used to create a patient-specific model of the maternal heart sounds. The mECG signal is highly detectable and can be used to segment the maternal heart sound signals and to create a model of the maternal heart sounds. The mECG position and/or the maternal heart sound model can be used to further improve fetal heart sound isolation from the maternal heart sound signals.

Regarding the detection of UA through the use of combined signal processing of signals from electrical property sensors and mechanical property sensors, determinations of UA from a combined analysis of these electrical and mechanical signals can produce improved overall detection. In examples, biopotential based UA determinations may suffer from false positives due to fetal movement, while mechanical (e.g. external pressure or strain) signal based UA determinations may suffer from low sensitivity. When both signals are available, the mechanical based UA determinations may be used to remove potential false positives from the biopotential based UA determination, to reduce the false positive rate, while benefitting from the higher sensitivity of the biopotential based UA determination.

Once UA events (e.g. contractions) are detected with the combined determination described above, segments of the respective biopotential and mechanical sensor signals can be extracted to create models of the maternal patient's contractions. These models, as described above, can be averages or aggregates of the extracted segments in either the time or frequency domain. These models develop and improve over time as more contracts are detected and newly extracted segments added to the models. These models can be used to further improve detection of new contractions in the individual biopotential and mechanical sensor signals.

As noted above, a variety of types of sensors may operate to serve as the mechanical motion sensors in the present disclosure. However, some types of sensors are better suited for detection of various physiological parameters than others. While a microphone can be used to detect fetal motion, mHR, or fHR, the collected sound waves are unsuited to detect uterine activity or contraction strength. Strain gauges are well suited to detect UA and contraction strength but are not able to be used to detect mHR, fHR, or fetal motion. Ultrasonic sensors and piezoelectric sensors can be used to detect all of the above noted fetal motion, mHR, fHR, UA, and contraction strength. However, ultrasonic sensors require an external power source to produce the emitted ultrasound signal and require a specialized acoustical interface with the skin of the maternal patient. Therefore, embodiments using ultrasound may impede the disposable and ease-of-use advantages of current embodiments of the monitoring patch device.

Embodiments of microphones, strain gauges, and piezoelectric sensors can all be printed using conductive inks, for example, silver-containing inks, in the manners as noted above with respect to the construction of other components of the patch. Therefore, microphones, strain gauges, and piezoelectric sensors may be incorporated into the patch without significant change to the manufacturing techniques currently used to construct the patch. In one embodiment, at least one, if not a plurality of piezoelectric sensors are incorporated into the patch as described above and signals representative of fetal motion, mHR, fHR, UA, and contraction strength collected therefrom. In another exemplary embodiment, at least one microphone and at least one strain gauge are incorporated into the patch as described above and signals representative of fetal motion, mHR, fHR, are collected from the at least one microphone, while signals representative of UA and contraction strength are collected from the at least one strain gauge.

In further embodiments, additional functionality may be added to the patch device as described herein with the incorporation of additional types of auxiliary sensors either into the patch substrate as described with respect to FIG. 2 or incorporated into the readout device 200 as described with respect to FIG. 3. These additional auxiliary sensors may include, but are not limited to, a temperature sensor or an $SpO_2$ sensor. The $SpO_2$ sensor uses a small light emitting diode (LED) to project red and/or infra-red light into the patient to measure the amount of light in this spectrum that is absorbed, producing an indication of the Oxygen saturation of the patient's blood. A temperature sensor may be a thermistor or a thermocouple and when placed in contact with the maternal patient's skin can be used to provide an ongoing presentation of maternal temperature, for example, to determine if the maternal patient is becoming too hot or too cold.

The controller (FIG. 1), the readout device (FIG. 3), or a communicatively connected computer may further use the measurement of the maternal skin temperature from the temperature sensor to provide an improved determination of maternal internal or core temperature. This temperature is more clinically relevant than skin temperature but is more challenging to estimate from skin temperature measurements. However, with the data collected from examples of the patch device as described herein, the independent collection of maternal heart rate and maternal skin temperature can be used to provide an improved estimation of maternal core temperature.

In still further embodiments, the controller (FIG. 1), the readout device (FIG. 3), or a communicatively connected computer may perform additional computational signal processing on the collected signals from the aforementioned sensors incorporated into the patch. This additional signal processing may be of the biopotential signals or may be of the sensors from the auxiliary sensors. Additional signal processing of the biopotential signals may be used to detect maternal or fetal EEG or to produce a more robust fECG or mECG analysis, including morphological analysis. Both biopotential signals and signals from the auxiliary sensor may be used to detect respiration rate, either as a motion artifact to biopotential signals or as respiratory sounds from a microphone, or respiratory abdominal movement in a piezoelectric sensor, a strain gauge, or an accelerometer. Additionally, signals from the auxiliary sensor suitable to detect fetal motion can also be further processed to detect the specific fetal motion of a kick to produce a kick count, which has been linked to an evaluation of fetal health.

Preferably, the readout device 200 comprises a wireless transmitter (e.g. according to the Bluetooth standard), operable to transmit the output of the readout device 200.

In some embodiments, the readout device 200 does not calculate any of the physiological data as noted above, but rather transmits raw or partially processed voltage and/or current data from the sensors, for processing by a further device into a suitable output (such as one, two, three, four or more of a fetal heart rate, fetal ECG, maternal heart rate, maternal ECG, or uterine activity).

Figure 4:
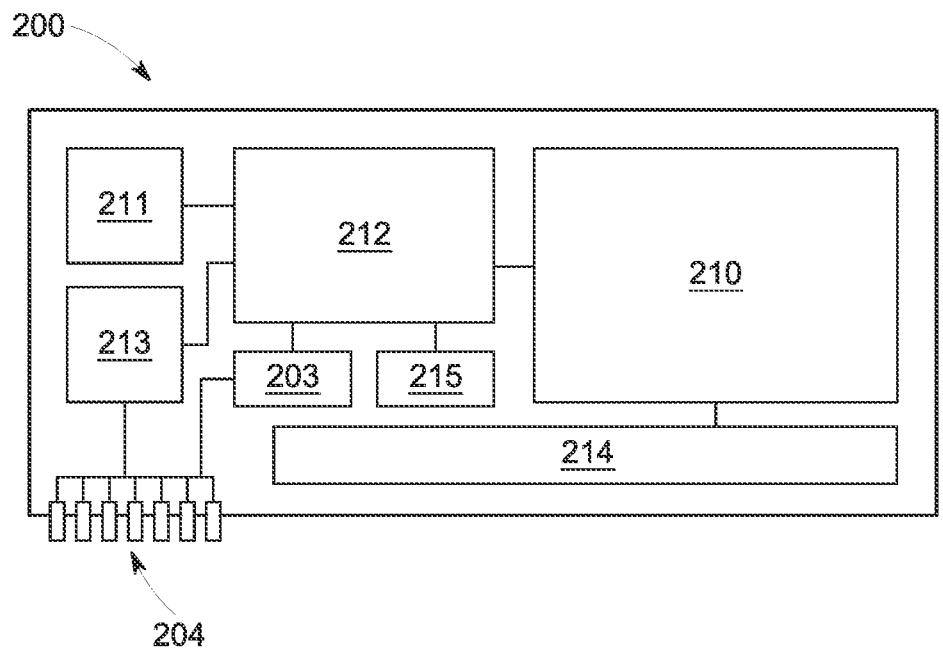
FIG. 4 is a block diagram of an exemplary embodiment of a readout device.

Referring to FIG. 4, a block diagram of a readout device 200 according to an embodiment is shown. The readout device 200 of FIG. 4 exemplarily presents a more detailed embodiment of the components of the controller as shown and described above with respect to FIG. 1. The readout device 200 comprises an electrical module unit 204, analog circuit 213, digital processor 212, wireless transmitter 211, security device 203, battery 210, and an inductive coil 214.

The analog circuit 213 includes an analog to digital converter, and receives the electrical signals from the electrodes and any electrical measurement signals from the mechanical sensors, and outputs a digitized version thereof, for processing by the digital signal processor. In some embodiments, the analog circuit 213 may include an amplifier and/or filter.

The processor 212 receives a digitized signal from the analog circuit 213, and preferably processes it to determine an output, as described already. The processor 212 subsequently outputs a signal to the wireless transmitter 211 for onward transmission, for example to a receiving and display station 300 according to an embodiment of the invention.

In order to maximize the battery life of the removable electronic device, it may be configured such that the power of the wireless transmitter is controlled based upon the signal strength index and/or bit error rate. This may greatly lengthen the monitoring period that can be carried under one single battery charge.

In some embodiments, one or more components of the device 200 may be combined, for example in a multi-chip module or system on a chip. For example, the processor 212 may comprise any combination of the analog circuit 213, the security device 203 and the wireless transmitter 211.

The electronic components of the readout device 200 are powered by an electrical power source, which is a battery 210 in this embodiment. In other embodiments, the electrical power source may comprise a capacitor. The inductive coil 214 is operative to charge the battery 210 or to power the readout device directly, optionally under the control of the processor 210.

The readout device 200 may be configured to detect electrophysiological signals between a pair of sensing electrodes, rather than simply between a sensing electrode and the common electrode. For example, the readout device 200 may be configured to detect electrophysiological signals between sensing electrodes 1 and 3 (i.e. horizontally across the abdomen in use). This allows a further channel of UA and fetal ECG to be provided. The advantages for UA are that the separation is relatively fixed between electrodes 1 and 3 and hence this offers the potential of indicating contraction strength. Furthermore, such a horizontal fECG channel (measured between sensing electrodes 1 and 3) allows breech and transverse presentations to be more carefully monitored. In addition, by providing this channel a further Maternal ECG channel can be generated that can be used for mECG removal, further reducing confusion between the mECG and fECG. The use of another mECG channel (for example, measured between sensing electrodes 1 and 3) can further reduce this confusion by providing an improved template for accurate mECG removal.

The readout device 200 may comprise sensors 215, which may comprise an inertial sensor such as an accelerometer and/or a gyroscope. Preferably, the sensors 215 comprise a one, two or three-axis accelerometer, and/or a one, two or three-axis gyroscope. The sensors 215 may be MEMS (micro-electromechanical systems) devices. The readout device 200 may comprise an inertial measurement unit. The accelerometers and gyroscopes may be used to track the movement of the readout device 200, thereby allowing both fetal ECG and electrohysterogram algorithms to differentiate between maternal/fetal movements and genuine contractions and fetal ECG signals and allowing to identify maternal pushing during the second stage of labor. A gyroscope can provide useful additional rotational information that an accelerometer cannot provide, thereby allowing further separation of fetal movement from the acquired data. This fetal movement is a highly useful indicator that provides further fetal well-being indication. Additionally, the use of the pair of devices allows separation of the maternal breathing signal which is a further indication of maternal health.

Figure 5:
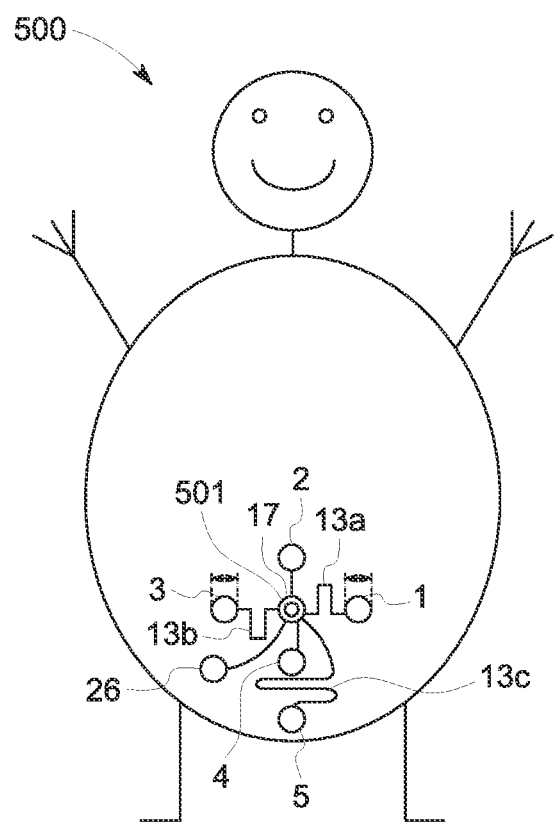
FIG. 5 is a schematic of a test subject and a patch in use on the test subject.

Referring to FIG. 5, a patch 150 according to an embodiment of the invention is shown in use, applied to the abdomen of a pregnant human subject 500. The skin is preferably prepared to ensure a good contact is made between each electrode and the skin, and gel is preferably applied to electrically couple the electrodes to the skin. The reference feature 17 of the patch is aligned with the umbilicus 501 of the subject 500, and the first sensing electrode 1 and drive electrode 4 are arranged on the abdomen on the median plane of the subject. The common electrode 5 is placed facing the symphis pubis, by extending the flexible substructure 13C if necessary. The patch 150 is comfortable and low profile, and relative movement of the electrodes (e.g. as a result of breathing and locomotion) is accommodated.

The integration of the readout circuit 200 and patch 150 allows the subject to move freely, without having to worry about leads and minimizing any deleterious cable noise that can arise due to triboelectric effects when leads are flexed. Furthermore, the short length of the connections to the readout circuit minimizes the potential for other sources of noise.

The readout device 200 preferably comprises a wireless transmitter (not shown) and is operable to wirelessly transmits the output, via the wireless transmitter, substantially in real-time, to a monitoring station that is operable to display the output. The readout device 200 is compatible with a number of monitoring stations but is preferably used with a receiving and display station 300 according to an embodiment of the invention.

Exemplary embodiments of the sensor patch and monitoring systems including the patch as described herein may be used to monitor maternal and fetal patients in a variety of settings. Embodiments may be used to monitor the progression of term and pre-term labor. However, other embodiments may be used to monitor neonatal fetal development, pre-term fetal development, and term fetal development. The disposability of the sensor patch embodiments and ease of use enable connection of such embodiments for patient monitoring over a short period of time, for example, an hour, during a routine pregnancy exam, while the design and wireless communication facilitate patient ambulation for monitoring of maternal and fetal patients under hospital observation. Still further embodiments, may be used for home monitoring and evaluation, for example during pre-labor, or early labor stages prior to the maternal patient arriving at a hospital, or for monitoring during home delivery.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives, and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A multi-sensor patch for simultaneous abdominal monitoring of maternal and fetal physiological data, the multi-sensor patch comprising:
   a multi-layer flexible substrate configured to be placed on the maternal abdomen and comprising a center region and a plurality of electrode regions, a conductive layer of the flexible substrate providing an electrical connection between each of the plurality of electrode regions and the center region;
   a plurality of electrodes formed into the flexible substrate with an electrode of the plurality of electrodes located in each of the electrode regions;
   at least one mechanical motion sensor connected to the multi-layer flexible substrate; and
   a module unit connected to the conductive layer at the center region, the module unit comprising a controller configured to receive biopotential physiological data from the plurality of electrodes and mechanical sensor data from the at least one mechanical motion sensor, to select segments of the biopotential physiological signals and mechanical sensor data and to create a patient specific model from the selected segments, and to calculate at least fetal heart rate (fHR), maternal heart rate (mHR), and uterine activity (UA) based on at least one of the biopotential physiological data and the mechanical sensor data compared to the patient specific model.

2. The multi-sensor patch of claim 1, further wherein the controller calculates a contraction strength from at least the mechanical sensor data.

3. The multi-sensor patch of claim 2, wherein the plurality of electrodes, the conductive layer, and the at least one mechanical motion sensor are printed from conductive ink.

4. The multi-sensor patch of claim 2, wherein the at least one mechanical motion sensor comprises a microphone.

5. The multi-sensor patch of claim 2, wherein the at least one mechanical motion sensor comprises a piezoelectric sensor.

6. The multi-sensor patch of claim 5, wherein the mechanical sensor data from the piezoelectric sensor is used by the controller in calculation of the fHR, mHR, and UA.

7. The multi-sensor patch of claim 2, wherein the at least one mechanical motion sensor comprises a strain gauge and wherein the controller uses the mechanical sensor data from the strain gauge to further calculate UA.

8. The multi-sensor patch of claim 7, wherein the at least one mechanical motion sensor further comprises a microphone, and wherein the controller uses the mechanical sensor data from the microphone to further calculate fHR and mHR.

9. The multi-sensor patch of claim 1, wherein at least one auxiliary sensor is located in the module unit.

10. The multi-sensor patch of claim 9, wherein the at least one auxiliary sensor located in the module unit comprises at least one of an ultrasound, a pulse oximeter, or a thermometer.

11. The multi-sensor patch of claim 1, wherein the controller further calculates a respiration rate from the biopotential physiological data and the mechanical sensor data.

12. The multi-sensor patch of claim 1, wherein the controller is further configured to receive an input selection from a user wherein upon receipt of such input selection, the controller switches from a calculation of UA that includes the biopotential physiological data to a calculation of UA based upon the mechanical sensor data while producing a calculated UA output in a real time or near real-time refresh rate.

13. The multi-sensor patch of claim 4, wherein the mechanical sensor data from the microphone sensor is used by the controller in calculation of the fHR and mHR.

14. The multi-sensor patch of claim 1, wherein the controller is further configured to receive an input selection from a user wherein upon receipt of such input selection, the controller switches from a calculation of UA that includes the biopotential physiological data to a calculation of UA based upon the mechanical sensor data while producing a calculated UA and mHR output in a real time or near real-time refresh rate.

15. The multi-sensor patch of claim 1, wherein at least one auxiliary sensor comprises a pulse oximeter and wherein physiological data from the pulse oximeter is used by the controller in combination with the biopotential physiological data to calculate maternal blood pressure.

16. The multi-sensor patch of claim 1, wherein the controller is further configured to identify fetal R-waves in the biopotential physiological signals and to select segments of the mechanical sensor data corresponding to fetal heart beats in the mechanical sensor data; and
wherein the patient specific model is a heartbeat model of a fetal patient.

17. The multi-sensor patch of claim 1, wherein the controller is further configured to compare the patient specific model to the mechanical sensor data to identify a search interval within a corresponding portion of the biopotential physiological signals for fECG detection.

18. The multi-sensor patch of claim 1, wherein the controller is further configured to compare the patient specific model to the mechanical sensor data to identify fetal heart motion and determine fetal heart rate.

19. The multi-sensor patch of claim 1, wherein the controller operates to identify maternal R-waves in the biopotential physiological signals and to select segments of the mechanical sensor data corresponding to maternal heart beats in the mechanical sensor data;
wherein the patient specific model is a heartbeat model of a maternal patient; and
wherein the controller operates to apply the patient specific model to the mechanical sensor data to remove maternal contribution to the mechanical sensor data.

20. The multi-sensor patch of claim 1, wherein the controller operates to compare the biopotential physiological signals and the mechanical sensor data to reject false positive detections of contractions in UA determinations from the biopotential physiological signals.

21. The multi-sensor patch of claim 1, wherein the controller conjunctly uses the biopotential physiological signals and the mechanical sensor data to detect uterine contraction.

22. The multi-sensor patch of claim 1, further comprising a temperature sensor and mechanical sensor data from the temperature sensor is used by the controller with the calculated mHR to determine an estimate of maternal core temperature.

* * * * *